US010694117B2

(12) United States Patent
Frangioni

(10) Patent No.: US 10,694,117 B2
(45) Date of Patent: Jun. 23, 2020

(54) MASKING APPROACH FOR IMAGING MULTI-PEAK FLUOROPHORES BY AN IMAGING SYSTEM

(71) Applicant: Curadel, LLC, Marlborough, MA (US)

(72) Inventor: John V. Frangioni, Wayland, MA (US)

(73) Assignee: Curadel, LLC, Marborough, MA (US)

( * ) Notice: Subject to any disclaimer, the term of this patent is extended or adjusted under 35 U.S.C. 154(b) by 0 days.

(21) Appl. No.: 16/002,432

(22) Filed: Jun. 7, 2018

(65) Prior Publication Data

US 2019/0379840 A1 Dec. 12, 2019

(51) Int. Cl.

| | |
|---|---|
| ***H04N 5/265*** | (2006.01) |
| ***H04N 5/33*** | (2006.01) |
| ***H04N 5/225*** | (2006.01) |
| ***H04N 5/445*** | (2011.01) |
| ***A61B 1/06*** | (2006.01) |
| ***A61B 1/313*** | (2006.01) |
| ***A61B 1/00*** | (2006.01) |

(52) U.S. Cl.

CPC .......... *H04N 5/265* (2013.01); *A61B 1/0005* (2013.01); *A61B 1/00006* (2013.01); *A61B 1/00009* (2013.01); *A61B 1/0638* (2013.01); *A61B 1/3132* (2013.01); *H04N 5/2256* (2013.01); *H04N 5/33* (2013.01); *H04N 5/44504* (2013.01); *A61B 1/0646* (2013.01); *H04N 2005/2255* (2013.01)

(58) Field of Classification Search

CPC combination set(s) only.
See application file for complete search history.

(56) References Cited

U.S. PATENT DOCUMENTS

| | | | | |
|---|---|---|---|---|
| 2009/0236541 | A1* | 9/2009 | Lomnes | A61B 1/043 250/458.1 |
| 2012/0025080 | A1 | 2/2012 | Liu et al. | |
| 2012/0123205 | A1* | 5/2012 | Nie | A61B 1/00174 600/109 |
| 2012/0257030 | A1 | 10/2012 | Lim et al. | |
| 2013/0041221 | A1 | 2/2013 | McDowell et al. | |

(Continued)

OTHER PUBLICATIONS

Montcel et al. "Two-peaked 5-ALA-induced PpIX fluorescence emission spectrum distinguishes lioblastomas from low grade gliomas and infiltrative component of glioblastomas" vol. 4, No. 4 / Biomedical Optics Express; Apr. 1, 2013; pp. 1-11.

(Continued)

*Primary Examiner* — Marnie A Matt
(74) *Attorney, Agent, or Firm* — Behmke Innovation Group LLC; James M. Behmke; Jonathon P. Western

(57) ABSTRACT

In one aspect, a visible light sensor of an imaging system captures a visible light image of a subject in which a fluorophore is present. The fluorophore has fluorescence emissions in the visible spectrum and in the near-infrared (NIR) spectrum. An NIR sensor of the imaging system captures an NIR image of the subject in which the fluorophore is present. The imaging system forms a combined image of the visible light image and the NIR image, in part by masking pixels of the visible light image with pixels of the NIR image that are associated with the fluorescence emission of the fluorophore in the NIR spectrum. The imaging system provides the combined image to an electronic display for display.

20 Claims, 6 Drawing Sheets

(56) References Cited

U.S. PATENT DOCUMENTS

| | | | | |
|---|---|---|---|---|
| 2015/0381909 | A1* | 12/2015 | Butte | H04N 5/332 348/68 |
| 2016/0187199 | A1* | 6/2016 | Brunk | G01J 3/2823 348/89 |
| 2017/0237958 | A1* | 8/2017 | Themelis | G02B 21/0028 348/34 |
| 2019/0191975 | A1* | 6/2019 | Talbert | G01J 3/10 |

OTHER PUBLICATIONS

Scott Prahl "Protoporphyrin IX Dimethyl Ester" https://omlc.org/spectra/PhotochemCAD/html/149.html; Jun. 2, 2017; pp. 1-4.

Markwardt et al. "405 nm versus 633 nm for protoporphyrin IX excitation in fluorescence-guided stereotactic biopsy of brain tumors" http://dx.doi.org/10.1002/jbio.201500195;2015; pp. 1-22.

International Search Report and Written Opinion dated Aug. 27, 2019 in connection with PCT/US2019/036002.

* cited by examiner

MASKING APPROACH FOR IMAGING MULTI-PEAK FLUOROPHORES BY AN IMAGING SYSTEM

TECHNICAL FIELD

The present disclosure relates generally to medical imaging systems and, more particularly, to a masking approach for imaging multi-peak fluorophores by an imaging system.

BACKGROUND

Today, various forms of imaging systems are used in the healthcare and research fields. In some cases, the imaging may be performed in vivo, i.e., within a living organism. Such imaging systems may include, for example, endoscopic imaging systems, laparoscopic imaging systems, open space imaging systems, and the like. In other cases, the imaging may be performed ex vivo, such as in the case of imaging biopsied tissue.

In general, fluorescence imaging entails capturing images of a fluorescent dye (e.g., a fluorophore) present within a subject. Such a dye may exhibit fluorescence, which is a mechanism by which a compound emits light at certain wavelengths when it is absorbs light of certain wavelengths. Often, the absorption wavelength is at a shorter wavelength than that of the emitted light during fluorescence.

In some cases, a fluorophore may exhibit multiple absorption and/or fluorescence peaks at different wavelengths. In such cases, the largest absorption and fluorescence peaks are typically selected for purposes of excitation and fluorescence imaging. This provides the greatest opportunity to detect the fluorophore within the subject undergoing imaging. While this approach may be suitable in many cases, it does so by effectively ignoring the secondary spectral peaks of the fluorophore, which may still be of use, from an image processing standpoint. Moreover, imaging of fluorophores emitting in the visible spectrum is problematic due to auto-fluorescence from endogenous molecules. Auto-fluorescence generates false-positive signals, which can be devastating if the visible fluorescence from the fluorophore is being used to resect tumors in the brain or elsewhere. In this case, otherwise healthy tissue would unnecessarily be targeted for resection. The present invention uses auto-fluorescence-free NIR signals to mask visible signals and thus improve both sensitivity and specificity of fluorescence imaging.

BRIEF DESCRIPTION OF THE DRAWINGS

The embodiments herein may be better understood by referring to the following description in conjunction with the accompanying drawings in which like reference numerals indicate identically or functionally similar elements, of which.

Figure 1:
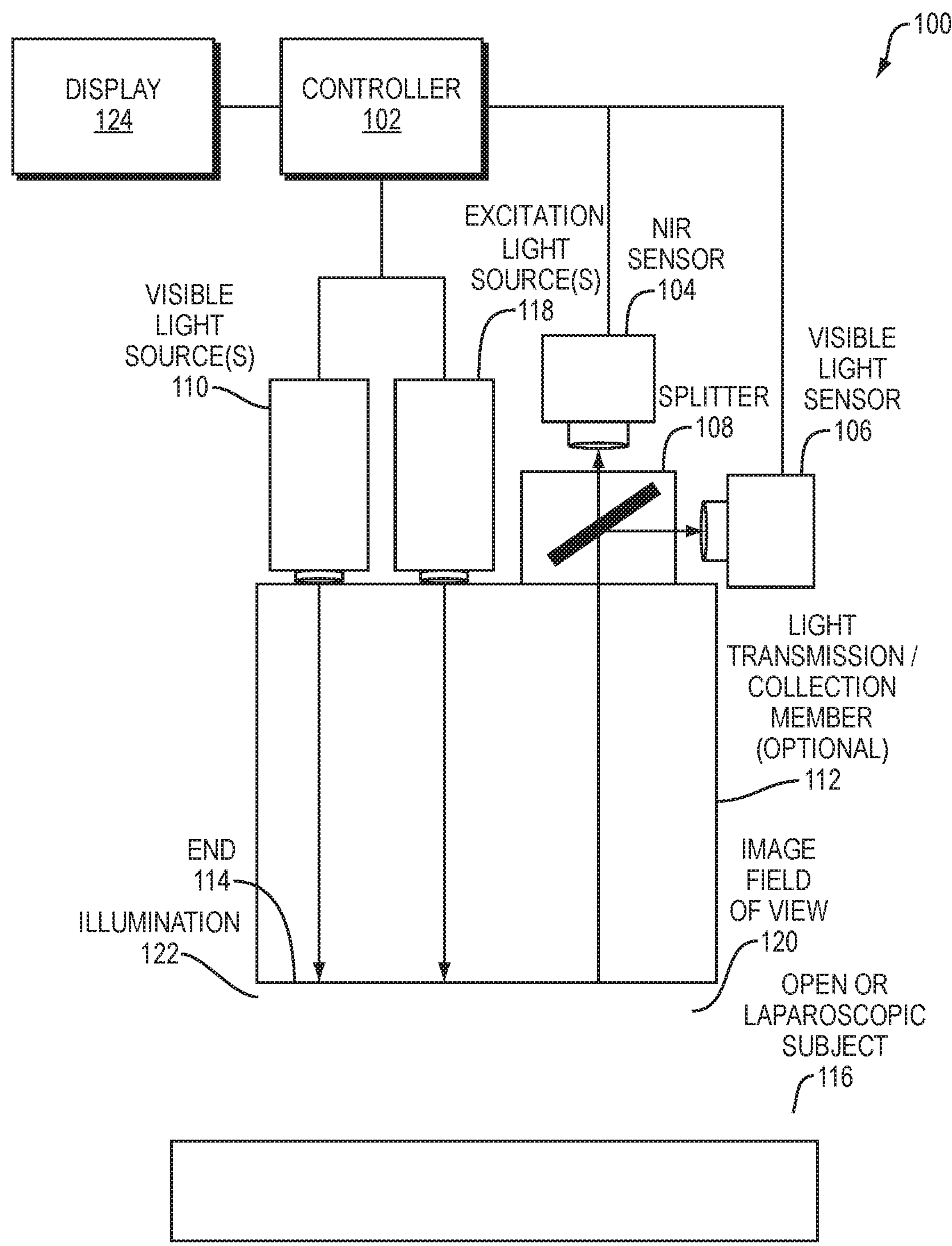
FIG. 1 illustrates an example embodiment of an imaging system.

In the figures, reference numbers refer to the same or equivalent parts of the present invention throughout the several figures of the drawing.

SUMMARY

According to the techniques described herein, a visible light sensor of an imaging system captures a visible light image of a subject in which a fluorophore is present. The fluorophore has fluorescence emission in both the visible spectrum and in the near-infrared (NIR) spectrum. An NIR sensor of the imaging system captures an NIR image of the subject in which the fluorophore is present. The imaging system forms a combined image of the visible light image and the NIR image, in part by masking pixels of the visible light image with pixels of the NIR image that are associated with the fluorescence emission of the fluorophore in the NIR spectrum. The imaging system provides the combined image to an electronic display for display.

In further embodiments, an imaging system is disclosed that includes a visible light sensor, a near-infrared (NIR) sensor, and a controller coupled to the visible light sensor and the NIR sensor. The controller includes a processor configured to execute a process and a memory configured to store the process. When executed, the process is configured to capture, by the visible light sensor, a visible light image of a subject in which a fluorophore is present. The fluorophore has fluorescence emissions in the visible spectrum and in the near-infrared (NIR) spectrum. The process is also configured to capture, by the NIR sensor, an NIR image of the subject in which the fluorophore is present. The process is further configured to form a combined image of the visible light image and the NIR image, in part by masking pixels of the visible light image with pixels of the NIR image that are associated with the fluorescence emission of the fluorophore in the NIR spectrum. The process is also configured to provide the combined image to an electronic display for display.

In yet another embodiment, a tangible, non-transitory, computer-readable medium storing program instructions that cause an imaging system to execute a process. The process includes capturing, by a visible light sensor of the imaging system, a visible light image of a subject in which a fluorophore is present. The fluorophore has fluorescence emissions in the visible spectrum and in the near-infrared (NIR) spectrum. The process also includes capturing, by an NIR sensor of the imaging system, an NIR image of the subject in which the fluorophore is present. The process further includes forming, by the imaging system, a combined image of the visible light image and the NIR image, in part by masking pixels of the visible light image with pixels of the NIR image that are associated with the fluorescence emission of the fluorophore in the NIR spectrum. The process also includes providing, by the imaging system, the combined image to an electronic display for display.

DETAILED DESCRIPTION

To provide an overall understanding of the invention, certain illustrative embodiments will now be described, including a system for generating superimposed circulatory and tissue images in video format. However, it will be understood that the methods and systems described herein can be suitably adapted to other medical imaging applications where visible light tissue images may be usefully displayed with diagnostic image information obtained from outside the visible light range and superimposed onto the visible light image. More generally, the methods and systems described herein may be adapted to any imaging application where a visible light image may be usefully displayed with a superimposed image captured from areas within the visible light image that are functionally marked to emit photons outside the visible light range by a dye or other material. For example, the systems and methods are applicable to a wide range of diagnostic or surgical applications where a target pathology, tissue type, or cell may be labeled with a fluorescent dye or other fluorescent substance. These and other applications of the systems described herein are intended to fall within the scope of the invention.

FIG. 1 shows an embodiment of an imaging system that may be used, for example, to image tissue either in vivo or ex vivo. The imaging system 100 may generally include a controller 102, a display 124, a near-infrared (NIR) sensor 104, one or more excitation light source(s) 118, a visible light sensor 106, a splitter mechanism 108, one or more visible light source(s) 110, and/or a light transmission/collection member 112. As would be appreciated, imaging system 100 may be adapted for any number of uses including, but not limited to, open surgical imaging, endoscopic or laparoscopic imaging, block face imaging (e.g., of a tissue sample), or the like. Examples of imaging system 100 include the FLARE® (FLuorescence-Assisted Resection and Exploration) imaging systems available from Curadel LLC, Marlborough, Mass., as well as any other type of optical imaging system.

In various embodiments, imaging system 100 may be configured to capture fluorescence images of a subject 116, such as organic tissue, using its sensors 104, 106. Prior to imaging subject 116 and/or during the imaging by imaging system 100, subject 116 may be injected with a fluorescent dye (e.g., a fluorophore) that is optically reactive when exposed to certain wavelengths of light. Generally, subject 116 may be any form of organic tissue in an open or laparoscopic/endoscopic setting, in various embodiments. For example, some dyes may be photo-reactive to certain wavelengths and emit light in the NIR range when exposed to illumination in this range. Leveraging this, imaging system 100 may capture contrasting images of subject 116 with NIR camera 104 capturing the phosphorescence/NIR images of subject 116 and the dye infused therein, and visible light sensor 106 capturing visible light images of subject 116. In general, near-infrared as used herein refers to the range of wavelengths between 660-900 nanometers ("nm").

Generally, and as described in more detail below, controller 102 may provide electronic control over illumination light source(s) 110, one or more excitation light source(s) 118, and sensors 104, 106, to capture the NIR and visible light images of subject 116, respectively. Controller 102 may also, in some embodiments, combine the imaging data from both types of captured images into a combined image. For example, such a combined image may present the NIR/fluorescence image data as an overlay for the visible image data, thereby providing a visual indication of the locations within subject 116 where the fluorescent dye is located. For example, certain dyes may bind to specific tumors, thereby facilitating visualization of the tumor within subject 116. In another example, such a dye may be injected into the blood stream of a live patient, thereby allowing the user of imaging system 100 to visualize the diffusing of the dye within subject 116. Once the NIR and visible light image data has been processed, controller 102 may provide the processed image data to a local or remote (e.g., connected via a network) display 124 for visualization and review by a user.

In some embodiments, illumination light source(s) 110 may include a visible light source that serves as a light source for visible light sensor 106. For example, the visible light source may be, for example, a near-infrared depleted white light source that provides illumination 122 to subject 116. Notably, this may be a one-hundred and fifty Watt halogen lamp with one or more filters to deplete wavelengths greater than 700 nm. Generally, any light source constrained to wavelengths between 400 nm and 700 nm may operate as the visible light source in light source(s) 110. In further embodiments, however, ambient lighting in the area may be used in part, or in whole, to provide the visible illumination to subject 116.

In some cases, imaging system 100 may be surrounded by an operating area (not shown) closed to ambient light. As will become clear from the following, many visible light sources such as incandescent lamps, halogen lamps, or daylight may include a broad spectrum of electromagnetic radiation that extends beyond the range of visible light detected by the human eye and into wavelengths used in the present system as a separate optical channel for generating diagnostic images. In order to effectively detect emission in these super-visible light wavelengths, it is preferred to enclose the surgical field, light source(s) 110, 118 and sensors 104, 106 in an area that is not exposed to broadband light sources. This may be achieved by using an operating room closed to external light sources, or by using a hood or other enclosure or covering for the surgical field that prevents invasion by unwanted spectrum. In other cases, this can be achieved simply by lowering the interfering light sources to a level where the imaging system in minimally affected. The visible light source of illumination light source(s) 110 may then serve as a light source for the visible light sensor 106, and also for provide conventional lighting within the visible light spectrum. As used herein, the term "operating area" is intended specifically to refer to an open surgical site that is closed to ambient light. Endoscopic or laparoscopic applications, as described below, are confined to surgical procedures within a closed body cavity, and do not include an operating area as that term is intended herein.

In addition to capturing visible light images of subject 116, NIR sensor 104 of imaging system 100 may capture NIR images of subject 116 (and the fluorescent dye present therein) as illuminated by an excitation light source 118 (e.g., by providing excitation illumination 122 to subject 116). For example, in certain applications, the excitation light source 118 and resulting emission from the dye present in subject 116 may have wavelengths near or below 700 nm, as with Cy5 dye, which emits light when excited at 650 nm. These near-red dyes may be used with the present system. However, this requires a visible light source 110 that excludes a portion of the visible light spectrum in which the dye operates, i.e., a far-red depleted white light source. Similarly, applications using quantum dots as a fluorescent substance may have absorption or emission wavelengths anywhere in the visible light spectrum, and a suitable visible light source 110 should be depleted at the wavelength(s) of interest. As such, the visible light source 110 should more generally be understood to be a source of light that includes some, but not necessarily all, of the wavelengths of visible light.

It should also be understood that, in a far-red imaging system or infrared imaging system such as those noted above, NIR sensor 104 described in the example embodiment will instead be a sensor sensitive to the emission wavelength of the injected dye or other fluorescent substance, and that other modifications to light sources, filters and other optics will be appropriate. Similar modifications may be made to isolate a band of wavelengths for dye excitation and emission anywhere within or outside the visible light range, provided that suitable optics, sensors, and dyes are available. Other fluorescent substances may also be used. For example, quantum dots may emit at visible light wavelengths, far-red, near-infrared, and infrared wavelengths, and at other wavelengths, typically in response to absorption below their emission wavelength. Suitable adjustments will be made to the excitation light source and the emission sensor, the NIR sensor in the example embodiment, for such applications. Sensors sensitive to far-red, near-infrared, and infrared wavelengths are commercially available.

In particular, excitation light source 118 may provide light at a wavelength that excites the dye present in subject 116. This may be, for example, a laser diode such as a 771 nm, 250 mW laser diode system, which may be obtained from Laser Components of Santa Rosa, Calif. Other single wavelength, narrowband, or broadband light sources may be used, provided they do not interfere with the visible light image captured by visible light sensor 106 (e.g., a video camera, etc.) or the emission wavelength of the dye. The near-infrared band is generally understood to include wavelengths between 700 nm and 1000 nm, and is a useful wavelength range for a number of readily available excitation light sources and dyes that may be used with the systems described herein. Suitable optical coupling and lenses may be provided to direct each of the visible light source and the excitation light source at an area of interest of subject 116.

Generally, splitter 108 may be operable to separate and direct the NIR and visible light received from the illuminated subject 116. For example, splitter 108 may include any number of filters and/or dichroic mirrors, to direct the fluorescence wavelengths towards NIR sensor 104 and the visible wavelengths towards visible light sensor 106 for capture. A number of arrangements of the sensors 104, 106 and splitter 108 are possible, and may involving reflecting or transmitting either the visible light image or the emission wavelength image.

In various embodiments, imaging system 100 may also include a light transmission/collection member 112 that conveys the light from light source(s) 110, 118 to the surface subject 116 and direct any light (e.g., reflected light, etc.) from subject 116 towards splitter 108 and sensors 104, 106. For example, light transmission/collection member 112 may include any number of fiber optics or other light guides/channels, to direct the illumination from light source(s) 110, 118 towards subject 116 and the captured light from subject 116 towards sensors 104, 106. In further embodiments, light source(s) 110 may be decoupled from light transmission/collection member 112, to provide illumination to subject 116 directly. In some embodiments, light transmission/collection member 112 may also include any number of lenses on its distal end 114, to transmit is light from light source(s) 110, 118 towards subject 116 and collect light from subject 116 for processing by sensors 104, 106.

Typically, the light provided by illumination light source(s) 110 and from excitation light source(s) 118 may be transmitted via different channels within light transmission/collection member 112. In other embodiments, they may be mixed. Note, also, that light transmission/collection member 112 may be optional, in some embodiments. For example, while endoscopic, laparoscopic, etc. application may employ member 112, other implementations, such as open surgical procedures, may not require member 112 and this component can be omitted.

NIR sensor 104 may be any form of sensor capable of capturing still images or moving images in the NIR portion of the spectrum. Notably, in some embodiments, NIR sensor 104 may be a still or moving image camera suitable for capturing images at the emission wavelength of the excited dye present in subject 116. The near-infrared camera may be, for example, an Orca-ER near-infrared camera with settings of gain 7, 2×2 binning, 640×480 pixel field of view, and an exposure time of 20 ms and an effective frame rate of fifteen frames per second. The Orca-ER is commercially available from Hamamatsu Photonic Systems of Bridgewater, N.J. It will be understood that the NIR sensor 104 in FIG. 1 is only an example. An infrared camera, a far-red camera, or some other camera or video device may be used to capture an emission wavelength image, with the camera and any associated filters selected according to the wavelength of a corresponding fluorescent substance used with the imaging system. As used herein, the term “emission wavelength camera” is intended to refer to any such camera that may be used with the systems described herein.

Visible light sensor 106 may be any form of sensor capable of capturing still images or video of subject 116 in the visible portion of the spectrum. In one embodiment, visible light sensor 106 may be a video camera suitable for capturing images of subject 116 in the visible light spectrum. In further embodiments, visible light sensor 106 may instead be a camera configured to take still images, as opposed to video. In one embodiment, sensor 106 is a color video camera model HV-D27, commercially available from Hitachi of Tarrytown, N.Y. For example, the video camera 106 may capture red-green-blue (RGB) images at thirty frames per second at a resolution of 640×480 pixels, or at any other number of frames or resolutions, as desired. In another example, camera 106 may be a high resolution Canon EOS 700 white light camera available from Canon, Melville, N.Y., although any other suitable white light camera can be used in other implementations. More generally, NIR sensor 104 and visible light sensor 106 may be any device capable of photonic detection and conversion to electronic images, including linear photodiode arrays, charge coupled device arrays, scanning photomultiplier tubes, and so forth.

As would be appreciated, NIR sensor 104 and visible light sensor 106 may be implemented in any number of ways. For example, in some cases, NIR sensor 104 and visible light sensor 106 may be implemented as separate cameras coupled to splitter 108. In other cases, however, NIR sensor 104 and visible light sensor 106 may be implemented as a single, multi-spectral camera capable of capturing both visible light and NIR images.

Display 124 may be a television, high-definition television, computer monitor, or other display configured to receive and render signals from controller 102. In some embodiments, display 124 may be a monocular or binocular eyepiece of the surgical microscope, with the near-infrared image superimposed on the visible light image in the eyepiece. In another embodiment, the eyepiece may use direct optical coupling of the surgical field to the eyepiece for conventional microscopic viewing, with the near-infrared image projected onto the eyepiece using, for example, heads-up display technology.

Generally, the controller 102 should be capable of digital filtering, gain adjustment, color balancing, and/or any other image processing functions. The image from the NIR sensor 104 is also typically shifted into the visible light range for display at some prominent wavelength, e.g., a color distinct from the visible light colors of the captured and/or displayed image data from sensor 106, so that a superimposed image will clearly depict the dye. The controller 102 may also perform image processing to combine the image from the NIR sensor 104 and the visible light sensor 106. Where the images are displayed side-by-side, this may simply entail rendering the images in suitable locations on a computer screen. Where the images are superimposed, a frame rate adjustment may be required. That is, if the visible light sensor 106 is capturing images at the conventional rate of thirty frames per second and the NIR sensor 104 is taking still pictures with an effective frame rate of fifteen frames per second, some additional processing may be required to render the superimposed images concurrently. This may entail either reducing the frame rate of the visible light sensor 106 to the frame rate of the NIR sensor 104 either by using every other frame of video data or averaging or otherwise interpolating video data to a slower frame rate. This may instead entail increasing the frame rate of the near-infrared image data, either by holding each frame of near-infrared data over successive frames of video data or extrapolating near-infrared data, such as by warping the near-infrared image according to changes in the video image or employing other known image processing techniques.

In one embodiment, the visible light source of light source(s) 110 is a near-infrared depleted visible light source, the excitation light source 118 is a 760 nm, 2.5 W laser diode, the dye is indocyanine green or ZW800-1, and imaging system 100 includes a 780 nm dichroic mirror (e.g., splitter 108) configured to transmit near-infrared light and reflect visible light, the a 781 nm longpass emission filter, and a 400 nm to 700 nm filter. The controller 102 comprises a processing circuit configured with software for image capture from the NIR sensor 104 and the visible light sensor 106, for making suitable color adjustment to the images from the NIR sensor 104, for making frame rate adjustments to the visible light sensor 106 image, and for combining the two images for superimposed display on the display 124.

The systems described above have numerous surgical applications. For example, the system may be deployed as an aid to cardiac surgery, where it may be used intraoperatively for direct visualization of cardiac blood flow, for direct visualization of myocardium at risk for infarction, and for image-guided placement of gene therapy and other medicinals to areas of interest. The system may be deployed as an aid to oncological surgery, where it may be used for direct visualization of tumor cells in a surgical field or for image-guided placement of gene therapy and other medicinals to an area of interest. The system may be deployed as an aid to general surgery for direct visualization of any function amenable to imaging with fluorescent dyes, including blood flow and tissue viability. In dermatology, the system may be used for sensitive detection of malignant cells or other skin conditions, and for non-surgical diagnosis of dermatological diseases using near-infrared ligands and/or antibodies.

In further embodiments, imaging system 100 may be adapted for use in an endoscope or laparoscope. Typically, a laparoscope is inserted into a body cavity through an incision, as distinguished from an endo scope that is inserted through an existing body opening such as the throat or rectum. A laparoscope has a different form factor than an endoscope, including different dimensional requirements. Furthermore, use of a laparoscope involves at least one additional step of making an incision into a body so that the laparoscope may be inserted into a body cavity. It will further be appreciated that the imaging system 100 may be used to simplify imaging devices other than endoscopes and laparoscopes, such as by providing an integrated, coaxial illumination and image capture device using the techniques described above.

In some embodiments, imaging system 100 may be configured to capture NIR images at different wavelengths, using any number of channels. For example, excitation light source(s) 118 may include lasers (e.g., laser diodes or other emitters) that illuminate the subject with light at different wavelengths. This may be done in an alternating or staggered manner, so as to capture the images under the different NIR illumination conditions via NIR sensor 104. Table 1 below shows an example of such a dual NIR illumination setup:

TABLE 1

| Type | Illumination | Light Collection |
|---|---|---|
| Color Video | 400-650 nm | 400-650 nm |
| NIR Channel 1 (NIR 1) | 665 ± 2 nm laser | 685-735 nm |
| NIR Channel 2 (NIR 2) | 760 ± 2 nm laser | ≥781 nm |

Figure 2:
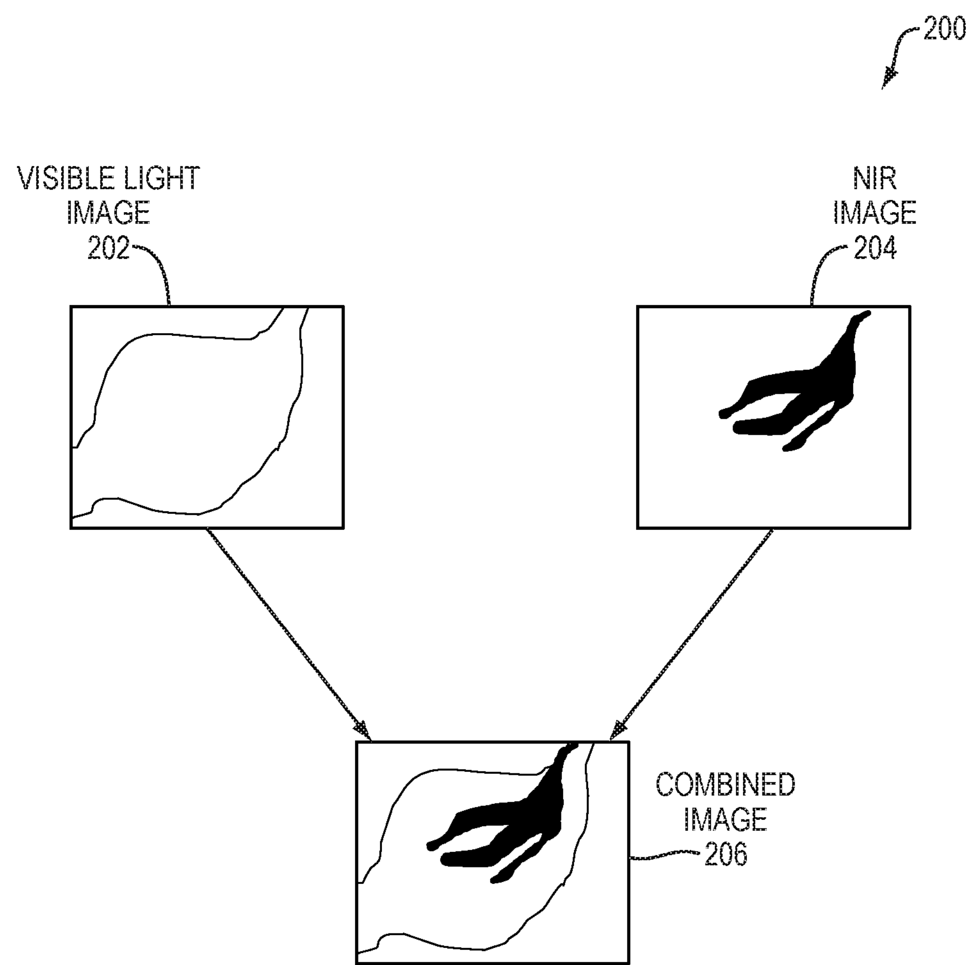
FIG. 2 illustrates the combination of visible and fluorescence images.

FIG. 2 shows an image displaying both a circulatory system and surrounding tissue. As described above, a visible light tissue image 202 is captured of tissue within a surgical field. As noted above, the visible light tissue image 202 may include a subset of visible light wavelengths when an optical channel for dye imaging includes a wavelength within the visible light range. A near-infrared image 204 is also captured of the same (or an overlapping) field of view of the surgical field. Although referred to here for convenience as a near-infrared image, it should be clear that the dye-based image 204 may also, or instead, employ other wavelengths, such as far-red or infrared wavelengths. The near-infrared image 204 may be shifted to a visible wavelength for display, preferably using a color that is prominent when superimposed on the visible light tissue image 202. The images 402, 404 may be frame-rate adjusted as appropriate for video display of the surgical field.

The images may be displayed separately as the visible light tissue image 202 and the near-infrared image 204. Or the images 202, 204 may be combined into a combined image 206 by the image processing unit described above. The combined image 206 may then be used as an aid to the procedures described above, or to any other surgical or diagnostic procedure that might benefit from the dye-based imaging techniques described herein.

Figure 3:
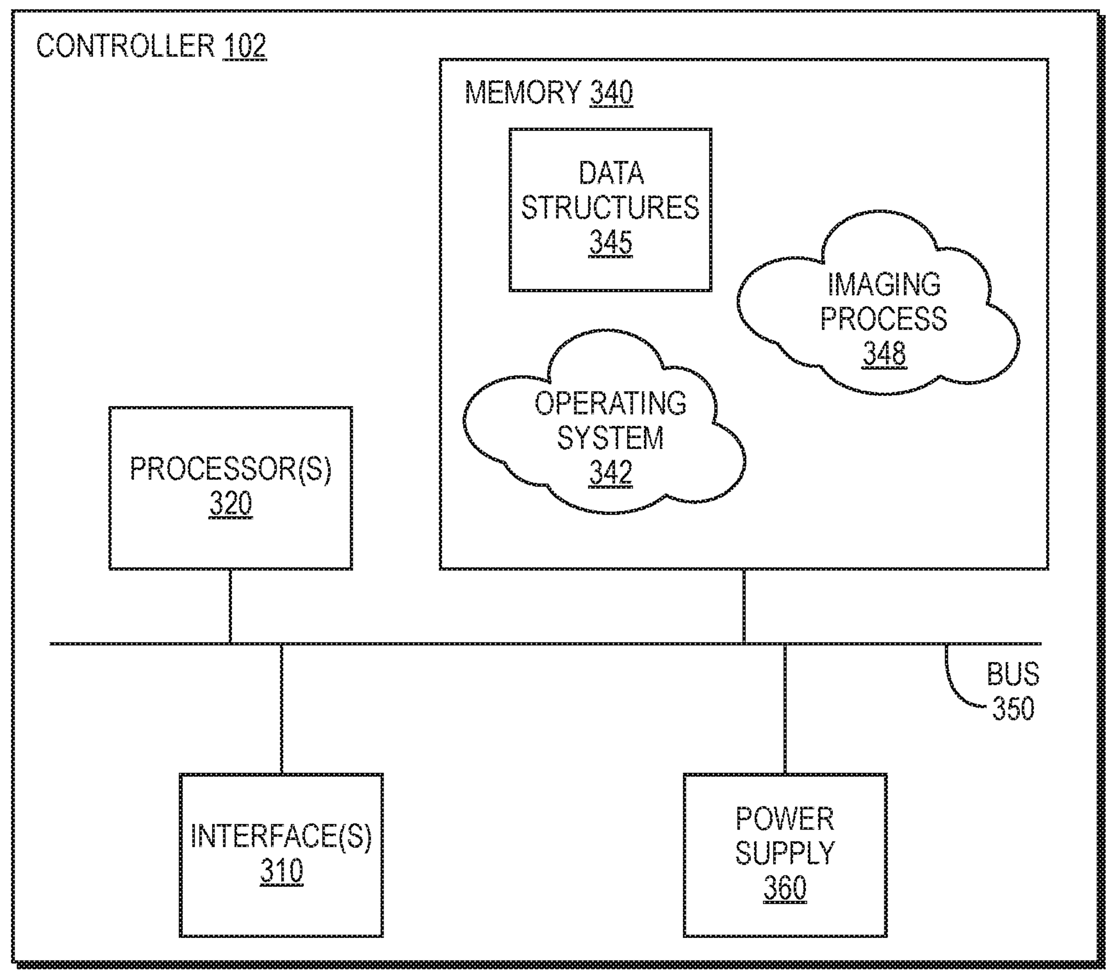
FIG. 3 illustrates an example controller for an imaging system.

FIG. 3 illustrates a controller 102 that may be used as part of any of the imaging systems/devices described herein, such as imaging system 100 in FIG. 1, according to various embodiments. As shown, controller 102 may comprise one or more network interfaces 310 (e.g., wired, wireless, etc.), at least one processor 320, and a memory 340 interconnected by a system bus 350, as well as a power supply 360 that provides electrical power to controller 102.

The interface(s) 310 contain the mechanical, electrical, and signaling circuitry for communicating data with other components of the imaging device/system and/or with other computing devices (e.g., via a computer network). For example, interface(s) 310 may be configured to transmit and/or receive data using a variety of different communication protocols via a communication network (e.g., to upload image data to a cloud service, to download software or data updates, etc.). In further examples, interface(s) 310 may be coupled to the various components of the imaging device to provide control commands to the sensor(s), lighting source(s), etc., of the imaging device and/or to receive captured image data from the sensor(s). Interface(s) 310 may also be in communication with an electronic display to display the resulting images after processing.

The memory 340 comprises a plurality of storage locations that are addressable by the processor 320 and the network interfaces 310 for storing software programs and data structures associated with the embodiments described herein. The processor 320 may comprise hardware elements or hardware logic adapted to execute the software programs and manipulate the data structures 345. An operating system 342, portions of which are typically resident in memory 340 and executed by the processor 320, functionally organizes the device by, inter alia, invoking operations in support of software processes and/or services executing on the device. These software processes and/or services may comprise an imaging process 348, as described herein.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules configured to operate in accordance with the techniques herein (e.g., according to the functionality of a similar process). Further, where certain processes have been shown separately, those skilled in the art will appreciate that processes may be routines or modules within other processes.

Imaging process 348, when executed by processor(s) 320, may be operable to perform any of the imaging functions described herein. For example, imaging process 348 may provide control over the components of the imaging device, to capture both color and fluorescence image data regarding organic tissue of interest. In turn, imaging process 348 may process the captured image data to form display data for display by an electronic display. For example, imaging process 348 may combine both the color and fluorescence data into an overlay image for display by the electronic display. Such a displayed image may be fully in color or at least partially in black and white or grayscale, in various embodiments.

Imaging of Multi-Peak Fluorophores

For purposes of fluorescence imaging of a subject, certain compounds may have two or more emission/fluorescence peaks at different wavelengths. For example, many tetrapyrroles, such as protoporphyrin IX (PpIX), exhibit such multi-peak fluorescence characteristics, when present within a subject. The general formula for PpIX is as follows:

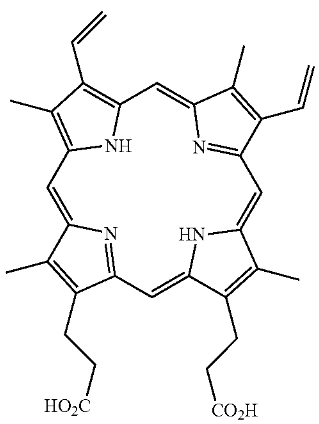

When PpIX is combined with iron, the resulting molecule is commonly referred to a 'heme.' Heme-containing proteins include hemoglobin, myoglobin, cytochrome c, and the like. PpIX can be synthesized biologically from 5-aminolevulinic acid (5-ALA) or 5-ALA derivatives, such as hexaminolevulinate HCl (Cysview), which are sometimes used as optical imaging agents/fluorescent substances, to visualize certain types of cancers via fluorescence imaging. FM-dyes also represent another class of fluorophores that exhibit multiple fluorescence peaks across the visible and NIR portions of the spectrum.

Figure 4A:
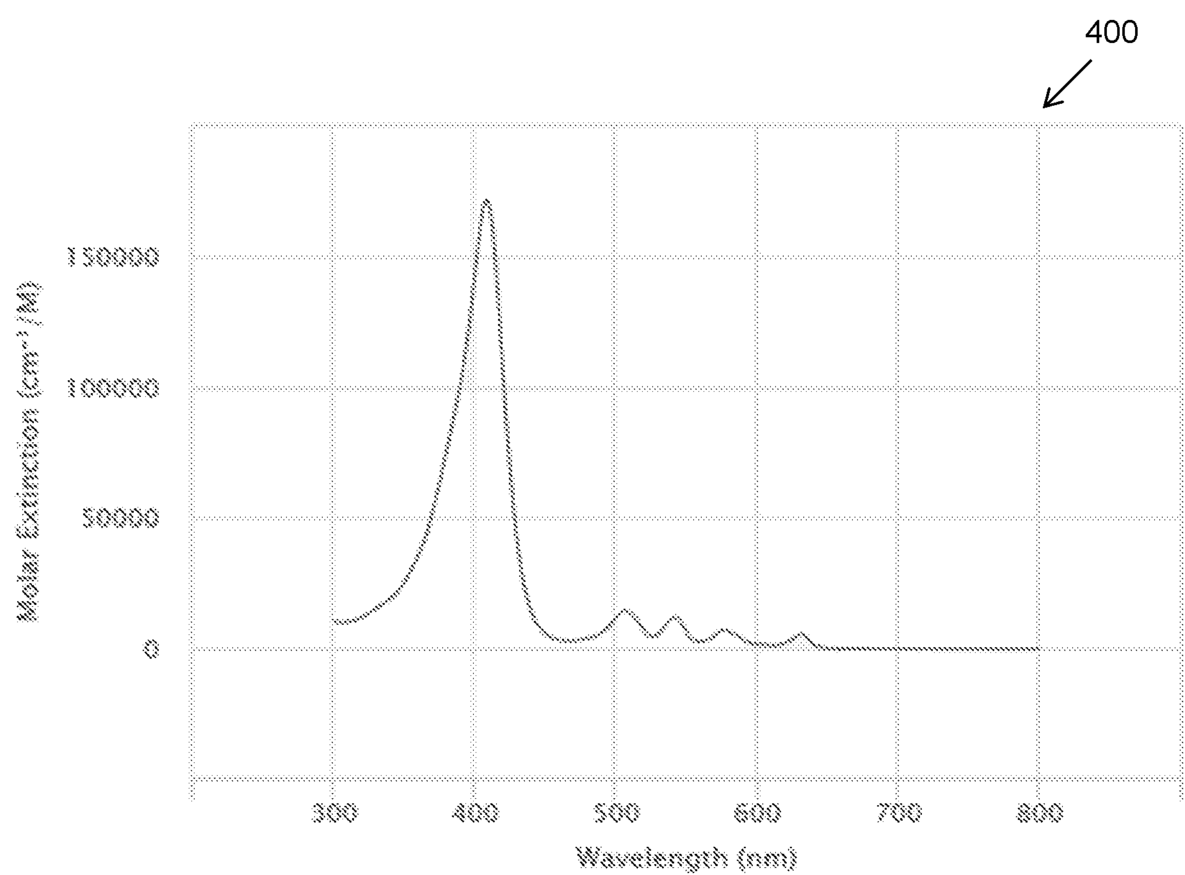
FIGS. 4A-4B illustrate example plots of the spectral characteristics protoporphyrin IX (PpIX)
Figure 4B:
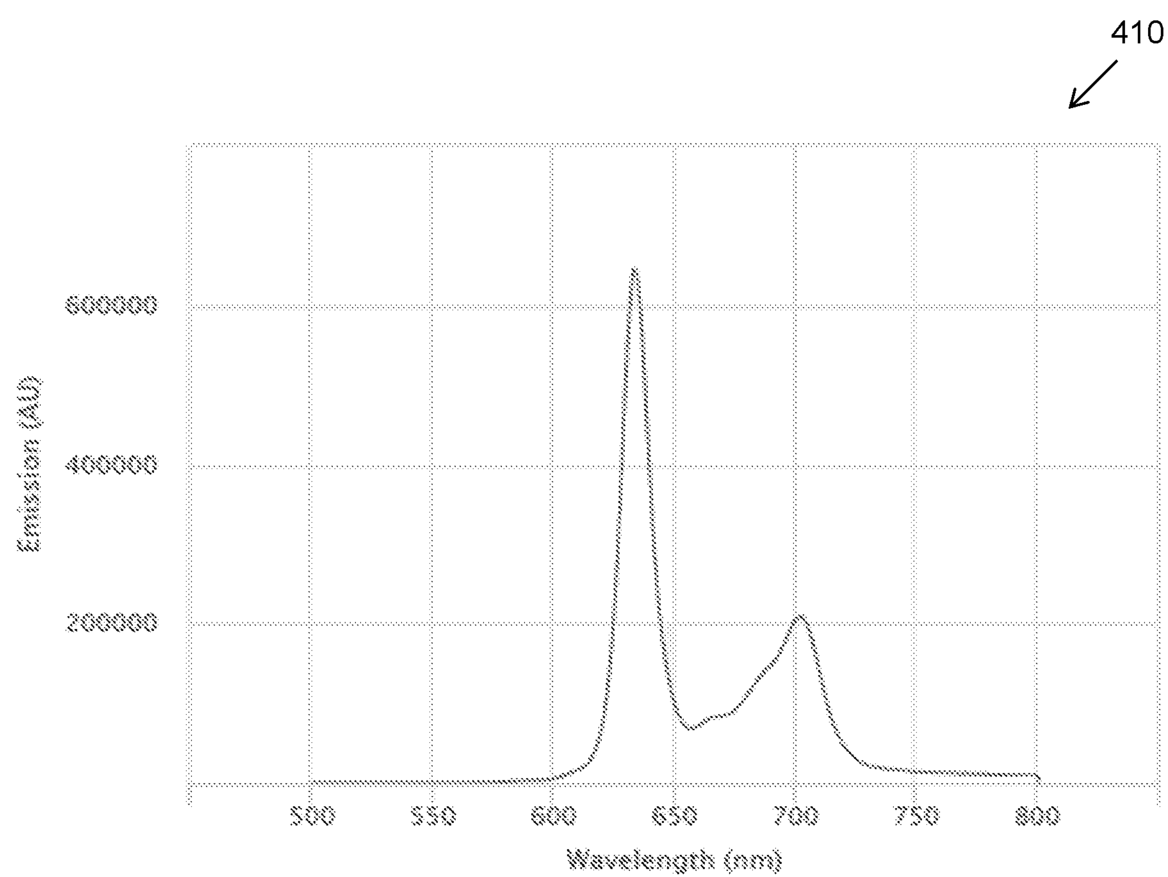

FIGS. 4A-4B illustrate example plots of the spectral characteristics of PpIX dimethyl ester in chloroform, which is a reasonable surrogate for its intracellular behavior, because it partitions into lipids. More specifically, plot 400 in FIG. 4A illustrates the absorption characteristics of PpIX, measured in terms of molar extinction, across various wavelengths. From this, it can be seen that PpIX has a primary absorption peak around approximately 405-408 nm, with several other minor absorption peaks at higher wavelengths. In FIG. 4B, plot 410 illustrates the fluorescence characteristics of PpIX in terms of emission at different wavelengths. As shown, PpIX has a primary emission peak in the visible red portion of the spectrum at approximately between 620 nm and 634 nm, depending on the medium. In addition, PpIX also exhibits a second, lesser emission peak in the NIR region of the spectrum somewhere between approximately 700-705 nm.

Typically, the primary emission peak of a fluorophore with multiple emission peaks is selected for purposes of detection during fluorescence imaging. For example, fluorescence imaging of PpIX is typically performed through the detection of its emission peak in the visible red portion of the spectrum, which is more than triple that of its emission peak in the NIR portion of the spectrum. However, imaging of fluorophores emitting in the visible spectrum is problematic due to auto-fluorescence from endogenous molecules. Auto-fluorescence generates false-positive signals, which can be devastating if the visible fluorescence from the fluorophore is being used to resect tumors in the brain or elsewhere. In this case, otherwise healthy tissue would unnecessarily be targeted for resection. The present invention uses auto-fluorescence-free NIR signals to mask visible signals and thus improve both sensitivity and specificity of fluorescence imaging.

In various embodiments, the techniques herein propose leveraging the detection of the fluorescence emissions of a fluorophore in different bands of the spectrum, which can be used to mask the color signal/image of the subject and remove unwanted background information from an image. For example, in the case of PpIX, adding the captured signals from both the visible red portion of the spectrum and the NIR portion of the spectrum on a pixel-by-pixel basis allows for improved fluorophore sensitivity and higher quality fluorescence imaging of the subject. As would be appreciated, some fluorophores may exhibit strong emission peaks in both the visible and NIR bands of the spectrum, while others may exhibit a flatter or less pronounced emission curve. While sharp emission peaks typically aid in fluorophore detection, the techniques herein can still be used for fluorophores that do not exhibit such pronounced emission peaks, so long as the fluorophore has fluorescence emissions in both bands.

Illustratively, the techniques described herein may be performed by hardware, software, and/or firmware, such as in accordance with the imaging process 348, which may include computer executable instructions executed by the processor 320, to perform functions relating to the techniques described herein.

Referring again to FIG. 1, imaging of a fluorophore within subject 116 that has fluorescence emissions in both the visible and non-visible portions of the spectrum (e.g., NIR, etc.) may proceed as follows. First, excitation light source(s) 118 may be configured to produce excitation illumination 122 in accordance with the spectral properties of the fluorophore being detected. For example, in the case of PpIX, excitation light source(s) 118 may comprise a blue laser that emits at, or about, 405 nm, in accordance with the spectral properties illustrated in plot 400 of FIG. 4A. As would be appreciated, other excitation light source(s) 118 may emit at different wavelengths, depending on the fluorophore. Next, sensors 104 and 106 may be configured to capture images of subject 116 across the ranges of wavelengths in which the fluorescence emissions of the fluorophore occur. In various embodiments, this may entail capturing both the visible light emissions of the fluorophore, via visible light sensor 106, as well as the NIR emissions of the fluorophore, via NIR sensor 104. For example, Table 2 below illustrates example parameters for light sources 110, 118, and sensors 104, 106 in a dual-NIR channel configuration, to perform imaging of PpIX in subject 116:

TABLE 2

| Type | Illumination | Light Collection |
|---|---|---|
| Color Video | 400-650 nm | 400-650 nm |
| NIR Channel 1 (NIR 1) | 405 ± 2 nm laser | 685-735 nm |
| NIR Channel 2 (NIR 2) | 760 ± 2 nm laser | ≥781 nm |

In such a configuration, a 420 nm longpass filter may also be placed in front of sensor(s) 104, 106, to filter out the 405 nm excitation.

According to various embodiments, controller 102 may operate light sources 110, 118 and sensors 104, 106, to capture images of subject 116 as follows:

Color Video Channel: this channel can be used to capture color video of subject 116 and, separately, the blue, green, and/or red pixels associated with the fluorescence emission of the fluorophore in subject 116. For example, the primary peak of PpIX is in the visible red portion of the visible spectrum and can be captured as red pixels, only. Of course, other fluorophores may have different fluorescence peaks or emissions that may instead be captured as blue or green pixels in the visible portion of the spectrum.

NIR Channel 1: this cannel can be used to capture images of the fluorescence emissions of the fluorophore in subject 116 that is in the NIR portion of the spectrum.

NIR Channel 2: this NIR channel, if used, is available for imaging anything else of interest in subject 116, such as blood vessels, nerves, etc.

In some embodiments, imaging system 100 can capture the different fluorescence emissions of the fluorophore in subject 116 simultaneously or nearly simultaneously. For example, in the case of PpIX imaging, system 100 may illuminate subject 116 with the 405 nm excitation laser of excitation light source(s) 118 and capture both the resulting red pixel information via from light sensor 106 and the resulting NIR image via NIR channel 1/NIR sensor 104. Doing so allows imaging system to detect both of the fluorescence peaks of the PpIX in subject 116.

In further embodiments, imaging system 100 may form a combined image for output to display 124 by using the captured image of the NIR fluorescence emission of the fluorophore to mask the corresponding visible light image of subject 116. Generally speaking, masking is an image processing technique that allows a portion of an image to be treated separately from that of its background. In the case of imaging a fluorophore with fluorescence emissions in both the visible spectrum and the NIR spectrum, such a masking may entail using the pixels indicative of the presence of the fluorophore in the NIR image, for example, pixels higher than some predefined signal-to-background ratio, to mask the corresponding pixels in the visible light image. For example, in the case of PpIX, the pixels in the NIR image indicative of the presence of the fluorophore can be used to mask the red pixels captured by imaging system 100 in the visible portion of the spectrum. Said differently, the NIR emission information can be used to mask the corresponding visible fluorescence emission information, when forming the combined image for display. As would be appreciated, such a masking improves the signal to background ratio in the combined image by removing unwanted background information, thereby resulting in a better fluorescence image of subject 116. Doing so also improves the absolute signal, because values from the visible and NIR pixels can be summed or otherwise combined mathematically.

Note that the masking approach detailed above can be adapted for any other fluorophore with fluorescence emissions in both the visible and NIR portions of the spectrum by masking the appropriate pixels of the visible light image. For example, other fluorophores may have fluorescence emissions in the visible green or blue portion of the spectrum. In such cases, the NIR emission information from the NIR image can be used to mask the corresponding green or blue pixels in the captured visible light image, accordingly.

Figure 5:
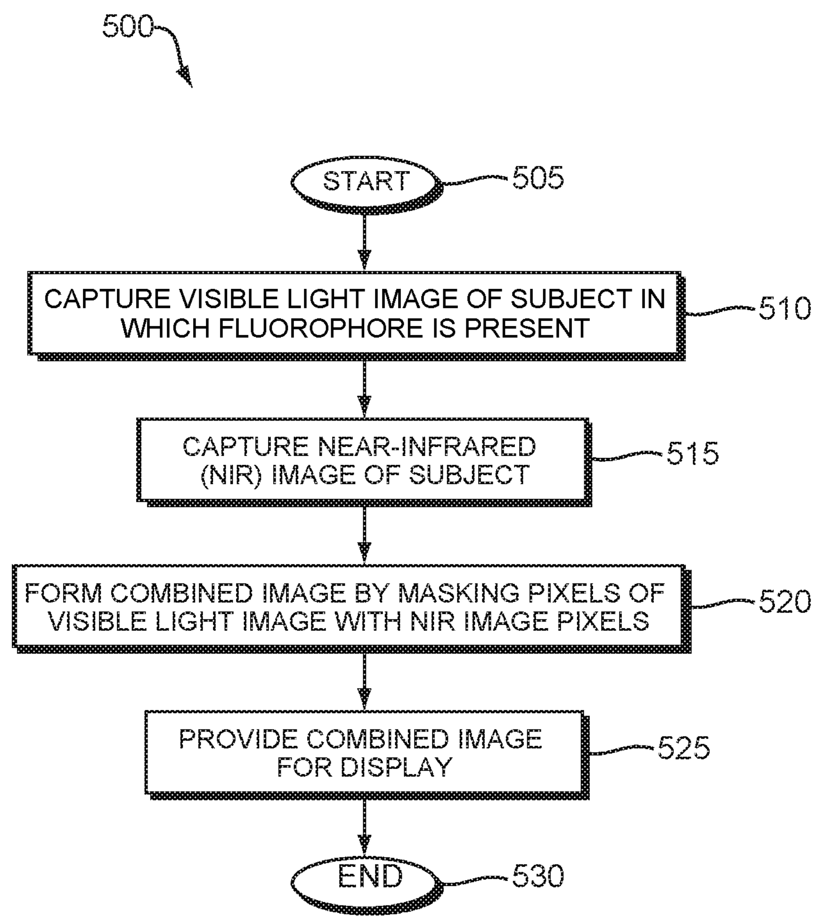
FIG. 5 illustrates an example simplified procedure for imaging a fluorophore.

FIG. 5 illustrates an example simplified procedure 500 for imaging a fluorophore, in accordance with one or more embodiments described herein. For example, a non-generic, specifically configured imaging system may perform procedure 500 by executing stored instructions (e.g., process 348), to implement the imaging techniques herein. Procedure 500 may start at step 505 and may continue on to step 510 where, as described in greater detail above, the imaging system may capture a visible light image of a subject in which a fluorophore is present. In various embodiments, the fluorophore may be a fluorophore that has fluorescence emissions in both the visible spectrum and in the near-infrared (NIR) spectrum. For example, tetrapyrroles, (e.g., PpIX, etc.), FM-dyes, and certain other compounds may have fluorescence emissions in both the visible portion of the spectrum and in the NIR portion of the spectrum. Note also that the magnitudes of the emissions can, and often do, differ. For example, PpIX and certain other fluorophores have much larger fluorescence peaks in the visible portion of the spectrum than in the NIR portion.

At step 515, as detailed above, an NIR sensor of the imaging system may capture an NIR image of the subject in which the fluorophore is present. As noted above, the fluorophore also has a fluorescence emission in the NIR range. In various embodiments, the imaging system may illuminate the subject with excitation light during capture of the NIR image and/or the visible light image, to capture information indicative of the location of the fluorophore within the subject. The characteristics of the excitation light can be selected, as desired, based on the spectral properties of the fluorophore in use. For example, a blue laser (e.g., a ~405 nm laser) may be used to induce fluorescence of PpIX or other tetrapyrroles. In some embodiments, the imaging system may perform steps 510 and 515 simultaneously, so as to acquire both the visible light image and NIR image at the same time. In other embodiments, the imaging system may acquire the images at different times (e.g., the visible light image, followed by the NIR image or vice-versa).

At step 520, the imaging system may form a combined image of the visible light image and the NIR image, as described in greater detail above. In various embodiments, the system may do so, in part, by masking pixels of the visible light image with pixels of the NIR image that are associated with the fluorescence emission of the fluorophore in the NIR spectrum. As would be appreciated, adding the signals associated with the visible light and NIR fluorescence emissions of the fluorophore for purposes of masking allows for a better signal to background ratio in the combined image, by removing unwanted background information. For example, if the fluorophore has a fluorescence emission in the visible red portion of the spectrum, the imaging system may mask the red pixels of the visible light image using the pixels from the NIR image that are associated with the fluorescence emission of the fluorophore in the NIR portion of the spectrum. Of course, a similar approach can be taken for green or blue pixels, depending on where the emission of the fluorophore in use lies within the visible portion of the spectrum.

At step 525, as detailed above, the imaging system may provide the combined image to an electronic display for display. In some embodiments, the imaging system may be in communication with the display (e.g., wirelessly, via a cable, via a network, etc.), allowing the combined image to be shown to a user. In part due to the masking in step 520, the locations within the subject at which the fluorophore is present will be highlighted to the user as part of the combined image. This is of particular use when the fluorophore concentrates in a certain organic structure of interest, such as a tumor. Procedure 500 then ends at step 530.

It should be noted that while certain steps within procedure 500 may be optional as described above, the steps shown in FIG. 5 are merely examples for illustration, and certain other steps may be included or excluded as desired. Further, while a particular order of the steps is shown, this ordering is merely illustrative, and any suitable arrangement of the steps may be utilized without departing from the scope of the embodiments herein.

It will be appreciated that the above functionality is merely illustrative, and that other dyes, imaging hardware, and optics may be usefully deployed with the imaging systems described herein. For example, an endoscopic tool may employ a still-image imaging system for diagnostic photography within a body cavity. Or any of the imaging systems may be used as described above with excitation and/or emission wavelengths in the far-red spectrum. Through minor adaptations that would be clear to one of ordinary skill in the art, the system could be configured to image two or more functions (i.e., tumor and blood flow) at the same time that a visible light image is captured by associating each function with a different dye having a different emission wavelength. Non-medical applications also exist for the imaging system. For example, dyes in a solution form may be sprayed on a mechanical component to identify oxidation, surface defects, or the like. Dyes could also be used to track gas, steam, or air flow through a pressurized system, and in particular to identify leaks around fittings and valves. These and other arrangements and adaptations of the subject matter discussed herein are intended to fall within the scope of the invention.

As will be appreciated, the above examples are intended only for the understanding of certain aspects of the techniques herein and are not limiting in nature. While the techniques are described primarily with respect to a particular device or system, the disclosed processes may be executed by other devices according to further implementations. For example, while the techniques herein are described primarily with respect to medical and research imaging, the techniques herein are not limited as such and can be adapted for use in other industries, as well. Further, while the techniques herein are described particularly in the context of NIR fluorescence imaging systems, the imaging techniques herein are not limited as such and can be applied within any number of different types of optical imaging systems.

The foregoing description has been directed to specific embodiments. It will be apparent, however, that other variations and modifications may be made to the described embodiments, with the attainment of some or all of their advantages. For instance, it is expressly contemplated that the components and/or elements described herein can be implemented as software being stored on a tangible (non-transitory) computer-readable medium (e.g., disks/CDs/RAM/EEPROM/etc.) having program instructions executing on a computer, hardware, firmware, or a combination thereof. Accordingly this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A method comprising:

capturing, by a visible light sensor of an imaging system, a visible light image of a subject in which a fluorophore is present, wherein the fluorophore has fluorescence emission in the visible spectrum and in the near-infrared (NIR) spectrum;

capturing, by an NIR sensor of the imaging system, an NIR image of the subject in which the fluorophore is present;

forming, by the imaging system, a combined image of the visible light image and the NIR image, in part by masking pixels of the visible light image with pixels of the NIR image that are associated with the fluorescence emission of the fluorophore in the NIR spectrum; and providing, by the imaging system, the combined image to an electronic display for display.

2. The method as in claim 1, further comprising:

illuminating, by an excitation light source of the imaging system, the subject with an excitation light, while capturing the NIR image of the subject.

3. The method as in claim 2, wherein the excitation light source is a blue laser.

4. The method as in claim 1, further comprising:

illuminating, by a visible light source of the imaging system, the subject with visible light, while capturing the visible light image.

5. The method as in claim 1, wherein the fluorophore comprises a tetrapyrrole.

6. The method as in claim 5, wherein the tetrapyrrole is protoporphyrin (PpIX).

7. The method as in claim 1, wherein masking the pixels of the visible light image comprises:

masking red pixels of the visible light image with the pixels of the NIR image that are associated with the fluorescence emission of the fluorophore in the NIR spectrum.

8. The method as in claim 7, wherein the fluorescence emission of the fluorophore in the visible spectrum is in a visible red portion of the visible spectrum.

9. The method as in claim 1, wherein masking the pixels of the visible light image comprises:

masking blue or green pixels of the visible light image with the pixels of the NIR image that are associated with the fluorescence emission of the fluorophore in the NIR spectrum.

10. The method as in claim 1, wherein the imaging system is coupled to an endoscope or laparoscope.

11. The method as in claim 1, wherein the visible light image and NIR image are open surgical images of the subject.

12. An imaging system comprising:

a visible light sensor;

a near-infrared (NIR) sensor; and a controller coupled to the visible light sensor and the NIR sensor, the controller comprising a processor configured to execute a process and a memory configured to store the process, the process when executed configured to:

capture, by the visible light sensor, a visible light image of a subject in which a fluorophore is present, wherein the fluorophore has fluorescence emissions in the visible spectrum and in the near-infrared (NIR) spectrum;

capture, by the NIR sensor, an NIR image of the subject in which the fluorophore is present;

form a combined image of the visible light image and the NIR image, in part by masking pixels of the visible light image with pixels of the NIR image that are associated with the fluorescence emission of the fluorophore in the NIR spectrum; and provide the combined image to an electronic display for display.

13. The imaging system as in claim 12, further comprising:

an excitation light source coupled to the controller that provides excitation illumination to the subject during capture of the NIR image by the NIR sensor.

14. The imaging system as in claim 12, wherein the fluorophore comprises a tetrapyrrole.

15. The imaging system as in claim 12, wherein the controller masks the pixels of the visible light image by:

masking red pixels of the visible light image with the pixels of the NIR image that are associated with the fluorescence emission of the fluorophore in the NIR spectrum.

16. The imaging system as in claim 15, wherein the fluorescence emission of the fluorophore in the visible spectrum is in a visible red portion of the visible spectrum.

17. The imaging system as in claim 12, wherein the controller masks the pixels of the visible light image by:

masking blue or green pixels of the visible light image with the pixels of the NIR image that are associated with the fluorescence emission of the fluorophore in the NIR spectrum.

18. The imaging system as in claim 12, further comprising:

an endoscopic or laparoscopic light transmission and collection member coupled to the sensors.

19. The imaging system as in claim 12, wherein the combined image is a video image.

20. A tangible, non-transitory, computer-readable medium storing program instructions that cause an imaging system to execute a process comprising:

capturing, by a visible light sensor of the imaging system, a visible light image of a subject in which a fluorophore is present, wherein the fluorophore has fluorescence emissions in the visible spectrum and in the near-infrared (NIR) spectrum;

capturing, by an NIR sensor of the imaging system, an NIR image of the subject in which the fluorophore is present;

forming, by the imaging system, a combined image of the visible light image and the NIR image, in part by masking pixels of the visible light image with pixels of the NIR image that are associated with the fluorescence emission of the fluorophore in the NIR spectrum; and providing, by the imaging system, the combined image to an electronic display for display.

* * * * *